US012357342B2

(12) United States Patent
Richter et al.

(10) Patent No.: US 12,357,342 B2
(45) Date of Patent: Jul. 15, 2025

(54) SCALPEL GUIDE

(71) Applicant: Medos International Sarl, LeLocle (CH)

(72) Inventors: Jorn Richter, Oberdorf (CH); Roman Lomeli, Raynham, MA (US); Philippe Lindenmann, Raynham, MA (US)

(73) Assignee: Medos International Sarl, LeLocie (CH)

( * ) Notice: Subject to any disclaimer, the term of this patent is extended or adjusted under 35 U.S.C. 154(b) by 403 days.

(21) Appl. No.: 18/061,779

(22) Filed: Dec. 5, 2022

(65) Prior Publication Data

US 2024/0173047 A1 May 30, 2024

Related U.S. Application Data

(60) Provisional application No. 63/385,288, filed on Nov. 29, 2022.

(51) Int. Cl.
 *A61B 17/3211* (2006.01)
 *A61B 17/32* (2006.01)
 *A61B 34/37* (2016.01)
(52) U.S. Cl.
 CPC .......... *A61B 17/3211* (2013.01); *A61B 34/37* (2016.02); *A61B 2017/320052* (2013.01)
(58) Field of Classification Search
 CPC ................ A61B 17/3211; A61B 34/30; A61B 2017/320052; A61B 17/32; A61B 17/32002; A61B 17/17
 See application file for complete search history.

(56) References Cited

U.S. PATENT DOCUMENTS

| 2015/0196365 | A1 | 7/2015 | Kostrzewski et al. |
| 2020/0113735 | A1* | 4/2020 | Kaplan ............... A61B 17/3211 |
| 2020/0323540 | A1* | 10/2020 | Kang ..................... A61B 34/20 |
| 2021/0282874 | A1 | 9/2021 | Hussain et al. |
| 2022/0167954 | A1* | 6/2022 | McGovern ......... A61B 17/3205 |

FOREIGN PATENT DOCUMENTS

| JP | 2015009137 A | 1/2015 |
| WO | WO2020/257115 A1 | 12/2020 |

OTHER PUBLICATIONS

International Search Report and Written Opinion dated Apr. 11, 2024 (PCT/EP2023/082503); 22 pgs.

* cited by examiner

*Primary Examiner* — Julian W Woo
*Assistant Examiner* — Khoa Tan Le
(74) *Attorney, Agent, or Firm* — Dunlap Codding, P.C.

(57) ABSTRACT

Scalpel guides for use with a tool guide of a surgical system are described. In one version, the scalpel guide includes a body defining a first guide slot sized and shaped to receive a body of a scalpel to guide a blade of the scalpel along a central axis without any lateral movement of the scalpel. The body also defines a second guide slot arranged such that the body of the scalpel inserted in the second guide slot is guided vertically by the sides of the second guide slot and allowed to move horizontally across the channel along the trajectory plane. Other versions of the scalpel guide are also described.

16 Claims, 4 Drawing Sheets

SCALPEL GUIDE

INCORPORATION BY REFERENCE

The present patent application claims priority to the provisional application U.S. Ser. No. 63/385,288, filed on Nov. 29, 2022; the entire contents of which are hereby expressly incorporated herein by reference.

BACKGROUND

A computer-assisted surgical system may include a robotic arm, controller, and navigational system. Robotic or robot-assisted surgeries have many associated advantages, particularly in terms of precise placement of surgical tools and/or implants. For example, during robot-assisted spine surgery, a trajectory is planned for a tool or series of tools attached to the robotic arm via a tool guide based on a surgical plan. During surgery, once the robotic arm has guided the tool guide to the planned trajectory, a first interaction with a patient is for a surgeon to create a skin incision at the intersection of the planned trajectory and the skin. Generally, this is done with a simple stab incision through a scalpel guide placed in the tool guide. However, the incision must be longer than a diameter of the tool guide, which is why the surgeon must manually enlarge the initial stab incision that was done through the scalpel guide which is disruptive of a flow of the surgical procedure.

SUMMARY

To overcome the need for this undesired manual enlargement, the presently disclosed systems, devices, and methods improve computer-assisted surgical systems, for instance, by providing various embodiments of a scalpel guide. In one embodiment, the scalpel guide allows precise marking of the intersection of a planned trajectory for a surgical procedure and the skin with a stab incision with a scalpel using a first guide slot, and a guided single-plane incision that is longer than a diameter of the tool guide using a second guide slot that allows a swiveling motion of the scalpel along the single-plane. In another embodiment, the scalpel guide includes a handle and guide prongs that guide the scalpel depending upon a setting of the handle to permit a stab incision and a guided single-plane incision to be made on a patient as described below.

The presently disclosed systems, methods, and devices are described for robotic surgical systems. Some embodiments of the invention provide a surgical robot (and optionally a navigation system) that utilizes a positioning system that allows movement of a tool support to a planned trajectory where a longitudinal axis of the tool support is coaxially aligned with the planned trajectory. The tool support has a first face, a second face, and an aperture from the first face to the second face. The aperture may be coaxially aligned with the longitudinal axis and sized and shaped to receive a scalpel guide.

In some embodiments, the scalpel guide has a body defining a first guide slot configured to receive a scalpel and guide a point of a blade of the scalpel to form a stab incision through a skin of a patient along the planned trajectory. The body may also have a second guide slot. The second guide slot may be sized and shaped to receive the scalpel and permit the scalpel to move laterally so as to permit the scalpel guided by the scalpel guide to move in an arc along a single plane thereby forming a single plane incision that is longer than a width of the second guide slot and/or an inside diameter of the tool support.

In other embodiments, a scalpel guide having a variable guiding system constructed in accordance with one embodiment of the present disclosure is described.

In another embodiment, a scalpel guide having an elongated portion with a trajectory marker formed therein is described. The trajectory marker indicates a planned trajectory. The scalpel guide may also have a guide slot sized and shaped to allow a scalpel to be moved laterally only along an arc on a single-plane that intersects the planned trajectory.

DETAILED DESCRIPTION

Figure 1:
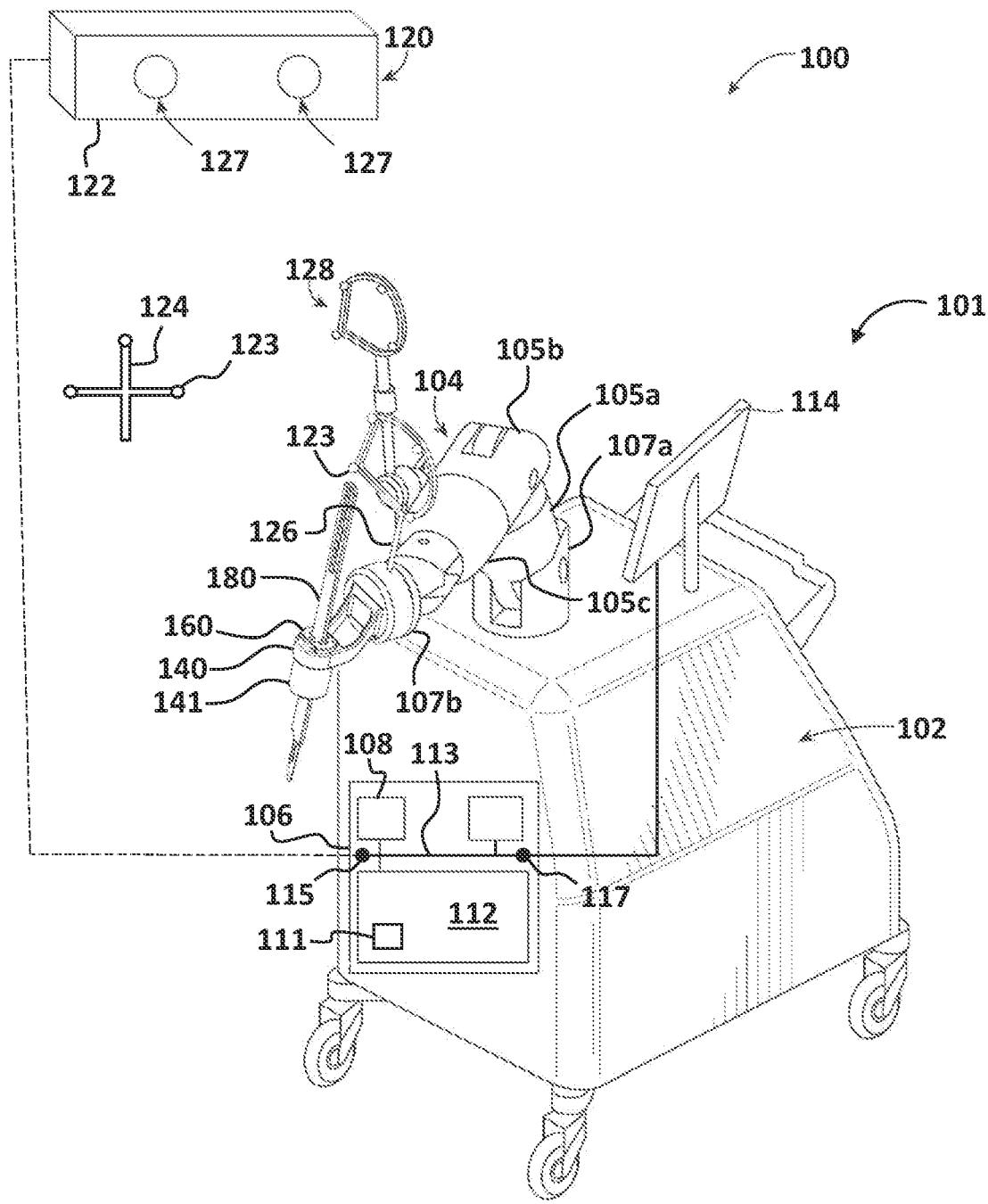
FIG. 1 shows a schematic of a computer-assisted surgical system including a robot base, a robotic arm, a tool guide attached to the robotic arm, a scalpel guide secured in the tool guide, the scalpel guide having a first guide slot and a second guide slot each adapted for receiving a scalpel in accordance with one embodiment of the present disclosure.
Figure 2:
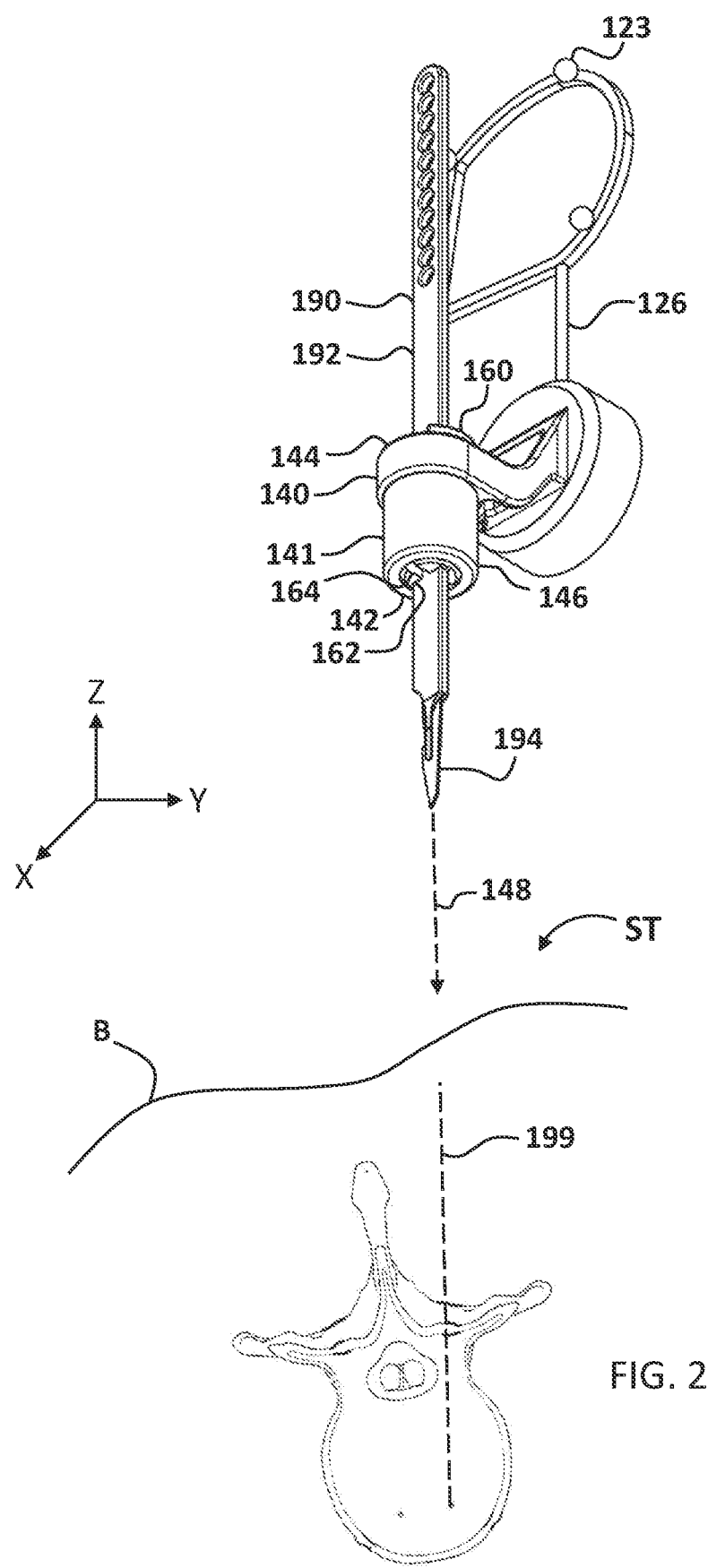
FIG. 2 is a bottom perspective view of the tool guide and scalpel guide of FIG. 1 with a scalpel inserted in the first guide slot of the scalpel guide such that a point of a blade of the scalpel is directed only along a planned trajectory.
Figures 3A, 3B:
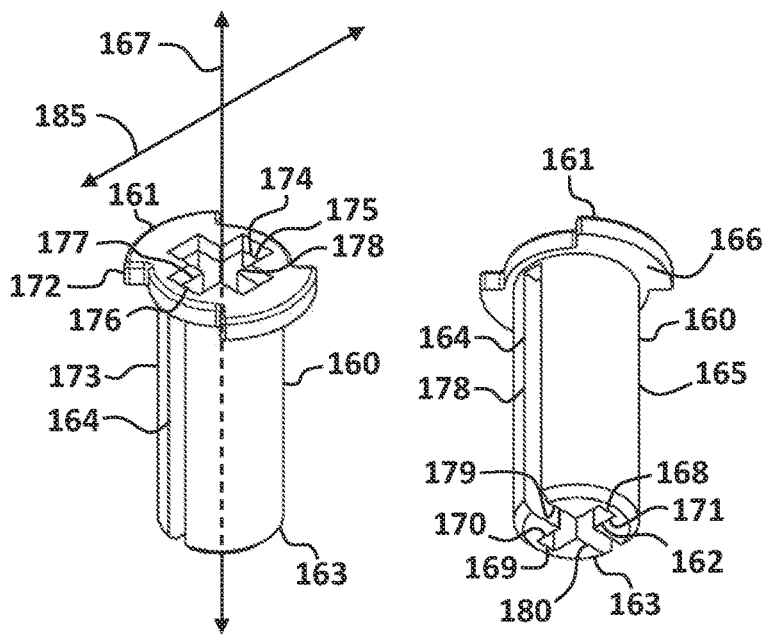
FIGS. 3A and 3B are perspective views of the scalpel guide of FIG. 1 showing the first guide slot and the second guide slot constructed in accordance with one embodiment of the present disclosure.

Before explaining at least one embodiment of the disclosure in detail, it is to be understood that the disclosure is not limited in its application to the details of construction, experiments, exemplary data, and/or the arrangement of the components set forth in the following description or illustrated in the drawings unless otherwise noted.

The systems and methods as described in the present disclosure are capable of other embodiments or of being practiced or carried out in various ways. Also, it is to be understood that the phraseology and terminology employed herein is for purposes of description, and should not be regarded as limiting.

The following detailed description refers to the accompanying drawings. The same reference numbers in different drawings may identify the same or similar elements.

As used in the description herein, the terms "comprises," "comprising," "includes," "including," "has," "having," or any other variations thereof, are intended to cover a non-exclusive inclusion. For example, unless otherwise noted, a process, method, article, or apparatus that comprises a list of elements is not necessarily limited to only those elements, but may also include other elements not expressly listed or inherent to such process, method, article, or apparatus.

Further, unless expressly stated to the contrary, "or" refers to an inclusive and not to an exclusive "or". For example, a condition A or B is satisfied by one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more, and the singular also includes the plural unless it is obvious that it is meant otherwise. Further, use of the term "plurality" is meant to convey "more than one" unless expressly stated to the contrary.

As used herein, any reference to "one embodiment," "an embodiment," "some embodiments," "one example," "for example," or "an example" means that a particular element, feature, structure or characteristic described in connection with the embodiment is included in at least one embodiment. The appearance of the phrase "in some embodiments" or "one example" in various places in the specification is not necessarily all referring to the same embodiment, for example.

Circuitry, as used herein, may be analog and/or digital components, or one or more suitably programmed processors (e.g., microprocessors) and associated hardware and software, or hardwired logic. Also, "components" may perform one or more functions. The term "component" may include hardware, such as a processor (e.g., microprocessor), a combination of hardware and software, and/or the like. Software may include one or more computer executable instructions that when executed by one or more components cause the component to perform a specified function. It should be understood that the algorithms described herein may be stored on one or more non-transitory memory. Exemplary non-transitory memory may include random access memory, read only memory, flash memory, and/or the like. Such non-transitory memory may be electrically based, optically based, and/or the like.

As used herein, the term "substantially" means that the subsequently described event or circumstance completely occurs or that the subsequently described event or circumstance occurs to a great extent or degree. As used herein the qualifier "substantially" is intended to include not only the exact value, amount, degree, orientation, or other qualified characteristic or value, but are intended to include some slight variations due to measuring error, control loop error, manufacturing tolerances, stress exerted on various parts or components, observer error, wear and tear, and combinations thereof. For example, when describing the longitudinal axis of the tool support substantially coaxially aligned with at least one planned trajectory, the term "substantially" refers to alignment within tracking tolerances.

Referring now to the drawings, and in particular to FIGS. 1-3B, shown therein is an overview of an exemplary computer-assisted surgical system 100. The computer-assisted surgical system 100 may be provided with a surgical robot 101 having a robot base 102 supporting a robotic arm 104 and a navigation system 120. A tool guide 140 may be attached to the robotic arm 104 and be configured to receive a scalpel guide 160 that is configured to receive a scalpel 180.

The robot base 102 is depicted as a mobile base, but stationary bases are also contemplated. The robotic arm 104 includes a plurality of arm segments 105a, 105b, 105c connected by rotatable or otherwise articulating joints and may be moved by actuation of the joints. One of the arms 105 forms a distal end 107b of the robotic arm 104. In the example shown in FIG. 1, the robotic arm 105c of the robotic arm 104 forms the distal end 107b. The robotic arm 104 also includes a proximal end 107a attached to and supported by the robot base 102, and the distal end 107b. The robotic arm 104 may be adapted to move in all six degrees of freedom during a surgical procedure. The robotic arm 104 may be configured for incremental changes (e.g., in each of the six degrees of freedom) to ensure the necessary precision during surgery. The robotic arm 104 may actively move about the joints to position the robotic arm 104 in a desired position relative to a patient (not depicted), or the robotic arm 104 may be set and locked into a position. For example, the present disclosure is contemplated to include use of tools by surgical robots, by users with some degree of robotic assistance, and without involvement of surgical robots or robotic assistance (e.g., once positioned and locked).

A control unit or controller 106 enables various features of the system 100, and performance of various methods disclosed herein in accordance with some embodiments of the present disclosure. In some embodiments, the controller 106 can control operation of the robotic arm 104 and associated navigational system(s) 120. In some embodiments, the control may comprise calibration of relative systems of coordinates, generation of planned trajectories, monitoring of position of various units of the surgical robot 101, and/or units functionally coupled thereto, implementation of safety protocols or limits, and the like. The controller 106 may be a system or systems able to embody and/or execute logic of processes described herein. The controller 106 may be configured to execute logic embodied in the form of software instructions and/or firmware. In some embodiments, the logic described herein may be executed in a stand-alone environment such as on the controller 106 and/or logic may be implemented in a networked environment such as a distributed system using multiple computers and/or processors.

The various embodiments of the present disclosure can be operational with other computing systems, environments, and/or configurations that can be suitable for use with the systems and methods of the invention and may comprise personal computers, server computers, laptop devices or handheld devices, and multiprocessor systems configured to execute logic embodied in the form of software instructions and/or firmware described herein. Additional examples comprise mobile devices, programmable consumer electronics, network PCs, minicomputers, mainframe computers, distributed computing environments that comprise any of the above systems or devices, and the like.

The controller 106 may include one or more processors 108 (hereinafter "processor 108"), one or more communication devices 110 (hereinafter "communication device 110"), one or more non-transitory memory 112 (hereinafter "memory 112") storing processor executable code and/or software application(s), such as application 111, and a system bus 113 that couples various components including the processor 108 to the memory 112, for example.

In general, the processor 108 refers to any computing processing unit or processing device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, or alternatively, the processor 108 may be an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors or processing units referred to herein can exploit nano-scale architectures such as, molecular and quantum-dot based transistors, switches and gates, in order to optimize space usage or enhance performance of the computing devices that can implement the various aspects of the subject invention. In some embodiments, processor 108 also can be implemented as a combination of computing processing units.

An external device 114 may communicate with the controller 106. The external device 114 may be a touch-screen display, a computing device, remote server, etc., configured to allow a surgeon or other user to input data directly into the controller 106. Such data may include patient information and/or surgical procedure information. The external device 114 may display information from the controller 106, such as alerts. Communication between the external device 114 and the controller 106 may be wireless or wired. The illustrated external device 114 is shown attached to the robot base 102, however, in some embodiments, the external device 114 may be The navigational system 120 may include a tracking unit 122. The system 100 is able to monitor, track, and/or determine changes in the relative position and/or orientation of one or more parts of the robotic arm 104, the tool guide 140, and/or a tool (such as the scalpel 180) inserted in the tool guide 140, as well as various parts of the patient's body B, within a common coordinate system by utilizing various types of fiducials 123 (e.g., multiple degree-of-freedom optical, inertial, and/or ultrasonic sensing devices), navigation systems (e.g., machine vision systems, charge coupled device cameras, tracker sensors, surface scanners, and/or range finders), anatomical computer models (e.g., magnetic resonance imaging scans of the lower lumbar region of the spine), data from previous surgical procedures and/or previously-performed surgical techniques (e.g., data recorded by the system 100 while performing earlier steps of a surgical procedure), and the like. Tracking may be performed in a number of ways, e.g., using stereoscopic optical detectors 127, ultrasonic detectors, sensors configured to receive position information from inertial measurement units, etc. Tracking in real time, in some embodiments, means high frequencies greater than twenty Hertz, in some embodiments in the range of one hundred to five hundred Hertz, with low latency, in some embodiments less than five milliseconds. Regardless of how it is gathered, position and orientation data may be transferred between components (e.g., to the controller 106) via any suitable connection, e.g., with wires or wirelessly using a low latency transfer protocol. The controller 106 may carry out real-time control algorithms at a reasonably high frequency with low additional latency to coordinate movement of the robotic arm 104 of the system 100. The tracking unit 122 may also include cameras, or use the stereoscopic optical detectors 127, to detect, for example, characteristics of the tool guide 140 attached to the robotic arm 104.

Fiducials 123 of the navigational system 120 may be attached to the navigation arrays (e.g., a first navigation array 124, a second navigational array 126, and an optional navigation array 128 (and/or other navigation arrays)). Fiducials 123 may be arranged in predetermined positions and orientations with respect to one another. The fiducials 123 may be aligned to lie in planes of known orientation (e.g., perpendicular planes, etc.) to enable setting of a Cartesian reference frame. The fiducials 123 may be positioned within a field of view of a navigation system 120 and may be identified in images captured by the navigation system 120. The fiducials 123 may be single-use reflective navigation markers. Exemplary fiducials 123 include infrared reflectors, light emitting diodes (LEDs), spherical reflective markers, blinking LEDs, augmented reality markers, and so forth. The first navigation array 124, second navigation array 126, and optional navigation array 128 may be or may include an inertial measurement unit (IMU), an accelerometer, a gyroscope, a magnetometer, other sensors, or combinations thereof. The sensors may transmit position and/or orientation information to the navigation system 120. In other embodiments, the sensors may be configured to transmit position and/or orientation information to an external controller which may be, for example, the controller 106.

The second navigation array 126 may be mounted on the robotic arm 104 or on the tool guide 140 and may be used to determine a position of the robotic arm 104 or a distal portion thereof (indicative of a position of the tool guide 140). The structure and operation of the second navigation array 126 may vary depending on the type of navigation system 120 used. In some embodiments, the second navigation array 126 may include one or more sphere-shaped or other fiducials 123 for use with an optical navigation system, for example, the second navigation array 126 illustrated in FIG. 2 with the spherical fiducial 123. The navigation system 120 facilitates registering and tracking of the position and/or orientation of the second navigation array 126 and, by extension, the tool guide 140 and a relative distance of the tool guide 140 to other objects in the operating room, e.g., a patient, a surgeon, etc. Position and/or orientation data may be gathered, determined, or otherwise handled by the navigation system 120 using registration/navigation techniques to determine coordinates of each navigation array and/or fiducial 123 within a coordinate system. These coordinates may be communicated to the controller 106 which uses the coordinates of each navigation array and/or fiducial 123 to calculate a position and orientation of the tool guide 140 in the coordinate system and a position of the tool guide 140 relative to the patient to facilitate articulation of the robotic arm 104.

The application 111 may configure the controller 106, or the processor 108 thereof, to perform the automated control of position of the robotic arm 104 in accordance with aspects of the invention. Such control can be enabled, at least in part, by the navigation system 120. In some embodiments, when the controller 106 is functionally coupled to the robotic arm 104, the application 111 can configure the controller 106 to perform the functionality described in the present disclosure. In some embodiments, the application 111 may be retained or stored in memory 112 as a group of computer-accessible instructions (for instance, computer-readable instructions, computer-executable instructions, or computer-readable computer-executable instructions). In some embodiments, the group of computer-accessible instructions can encode the methods of the presently disclosed inventive concepts. In some embodiments, the application 111 may encode various formalisms (e.g., image segmentation) for computer vision tracking using the navigation system 120. In some embodiments, the application 111 may be a compiled instance of such computer-accessible instructions stored in the memory 112, a linked instance of such computer-accessible instructions, a compiled and linked instance of such computer-executable instructions, or an otherwise executable instance of the group of computer-accessible instructions.

The memory 112 may be any available media that is accessible by the controller 106 and comprises, for example and not meant to be limiting, both volatile and non-volatile media, removable and non-removable media. In some embodiments, the memory 112 comprises computer readable media in the form of volatile memory, such as random access memory (RAM), and/or non-volatile memory, such as read only memory (ROM). In some embodiments, the memory 112 may store data (such as a group of tokens employed for code buffers) and/or program modules such as the application 111 that are immediately accessible to, and/or are presently operated-on by the controller 106. In some embodiments, the memory may store an operating system (not shown) such as Windows operating system, Unix, Linux, Symbian, Android, Apple iOS operating system, Chromium, and substantially any operating system for wireless computing devices or tethered computing devices. Apple® is a trademark of Apple Computer, Inc., registered in the United States and other countries. iOS® is a registered trademark of Cisco and used under license by Apple Inc. Microsoft® and Windows® are either registered trademarks or trademarks of Microsoft Corporation in the United States and/or other countries. Android® and Chrome® operating system are registered trademarks of Google Inc. Symbian® is a registered trademark of Symbian Ltd. Linux® is a registered trademark of Linus Torvalds. UNIX® is a registered trademark of The Open Group.

In some embodiments, the memory 112 may be a mass storage device which can provide non-volatile storage of computer code (e.g., computer-executable instructions such as the application 111), computer-readable instructions, data structures, program modules, and other data for the controller 106. For instance, in some embodiments, the memory 112 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

In some embodiments, optionally, any number of program modules can be stored on the memory 112, including by way of example, the operating system, and a tracking software (not shown). In some embodiments, data and code (for example, computer-executable instructions, patient-specific trajectories, and patient anatomical data) may be retained and stored on the memory 112. In some embodiments, data and/or code, may be stored in any of one or more databases known in the art. Examples of such databases comprise, DB2®, Microsoft® Access, Microsoft® SQL Server, Oracle®, mySQL, PostgreSQL, and the like. Further examples include membase databases and flat file databases. The databases can be centralized or distributed across multiple systems.

DB2® is a registered trademark of IBM in the United States.

Microsoft®, Microsoft® Access®, and Microsoft® SQL Server™ are either registered trademarks or trademarks of Microsoft Corporation in the United States and/or other countries.

Oracle® is a registered trademark of Oracle Corporation and/or its affiliates.

MySQL® is a registered trademark of MySQL AB in the United States, the European Union and other countries.

PostgreSQL® and the PostgreSQL® logo are trademarks or registered trademarks of The PostgreSQL Global Development Group, in the U.S. and other countries.

In some embodiments, the user (for example, a surgeon or other user, or equipment) can enter commands and information into the controller 106 via the external device 114 using an input device (not shown). Examples of such input devices include, but are not limited to, a keyboard, a pointing device (for example, a mouse), a microphone, a joystick, a scanner (for example, a barcode scanner), a reader device such as a radiofrequency identification (RFID) readers or magnetic stripe readers, gesture-based input devices such as tactile input devices (for example, touch screens, gloves and other body coverings or wearable devices), speech recognition devices, or natural interfaces, and the like.

In some embodiments, the external device 114 may be functionally coupled to the system bus 113 via an interface 116. In some embodiments, the controller 106 may be configured to have more than one external device 114. For example, in some embodiments, the external device 114 may be a monitor, a liquid crystal display, or a projector. Further, in addition to the external device 114, some embodiments may include other output peripheral devices that can comprise components such as speakers (not shown) and a printer (not shown) capable of being connected to the controller 106 via interface 116. In some embodiments, a pointing device, may be either tethered to, or wirelessly coupled to the controller 106 to receive input from the user. In some embodiments, any step and/or result of the methods can be output in any form to an output device such as the external device 114. In some embodiments, the output can be any form of visual representation, including, but not limited to, textual, graphical, animation, audio, tactile, and the like.

In certain embodiments, one or more cameras may be contained or functionally coupled to the navigation system 120, which is functionally coupled to the system bus 113 via an input/output interface 115. Such functional coupling can permit the one or more camera(s) to be coupled to other functional elements of the controller 106. In one embodiment, the input/output interface 115, at least a portion of the system bus 113, and the memory 112 can embody a frame grabber unit that can permit receiving imaging data acquired by at least one of the one or more cameras. In some embodiments, the frame grabber can be an analog frame grabber, a digital frame grabber, or a combination thereof. In some embodiments, where the frame grabber is an analog frame grabber, the processor 108 can provide analog-to-digital conversion functionality and decoder functionality to enable the frame grabber to operate with medical imaging data. Further, in some embodiments, the input/output interface 115 can include circuitry to collect the analog signal received from at least one camera of the one or more cameras. In some embodiments, in response to execution by processor 108, the application 111 may operate the frame grabber to receive imaging data in accordance with various aspects described herein.

The tool guide 140 may be coupled to the robotic arm 104 using conventional means known in the art, such as a threaded connection. As can be appreciated, there should be no play between the tool guide 140 and robotic arm 104.

While the system 100 may utilize tool guides of various shapes, sizes, and functionalities, the depicted tool guide 140 has a tool support 141 having an aperture 142 (see FIG. 2) for retaining, guiding, positioning, supporting, and/or locating at least one tool or guide such as the scalpel guide 160. Advantageously, the tool support 141 may be configured to guide, position, support, or locate a series of tools used in a surgical procedure, such as spinal surgery, with respect to a surgical site ST. The robotic arm 104 may be configured to help a user (e.g., a surgeon) guide, position, support, or locate the tools and/or guides along at least one planned trajectory 199 using the tool guide 140. Exemplary tools include, but are not limited to, a dilator having a dilator tip (e.g., sharp or blunt), a probe, a cutting instrument, a tap, a screw, etc. The cutting instrument may be, for example, a drill, saw blade, burr, reamer, mill, scalpel blade, or any other implement that could cut bone or other tissue and is appropriate for use in a particular surgical procedure. The tools may be secured in the tool guide 140 using a locking mechanism (not shown). The locking mechanism may be a slider locking mechanism or other feature, for instance.

In some embodiments, the tool guide 140 includes the tool support 141 having the aperture 142 extending from a first face 144 of the tool support 141 to a second face 146 of the tool support 141 and has a longitudinal axis 148 that extends through a center of the aperture 142. In some embodiments, the tool support 141 can be a tube.

As described herein, some embodiments include the controller 106 that can control operation of the robotic arm 104. The controller 106 may be configured to execute the application 111 to control the robotic arm 104. In some embodiments, the application 111, in response to execution by the processor 108, can utilize trajectories (such as, tip and tail coordinates) that can be planned and/or configured remotely or locally before and/or during a surgical procedure. A trajectory that has been planned before or during the surgical procedure may be referred to herein as a "planned trajectory" such as the planned trajectory 199. In an additional or alternative aspect, in response to execution by the processor 108, the application 111 may be configured to implement one or more of the methods described herein in the controller 106 to cause movement of the robotic arm 104 according to one or more planned trajectories such as planned trajectory 199. It should be noted that for a spine surgery there are multiple planned trajectories. It would be common to have six trajectories (three pairs of two trajectories, i.e., one pair of trajectories for each vertebral body involved in the surgery), for instance. In some embodiments, four trajectories may be used for fusing two vertebral bodies together. Each planned trajectory would be identified in the application 111 and may be planned to be executed in a certain order. For instance, in an exemplary surgical procedure for fusing first and second vertebral bodies together, four planned trajectories would be used and may be identified as a first planned trajectory, a second planned trajectory, a third planned trajectory, and a fourth planned trajectory. A user, such as a surgeon, may plan to work on one side of the patient first. For example, the first planned trajectory would be directed to a first side of the first vertebral body and the second planned trajectory would be directed to a first side of the second vertebral body. The surgeon may then plan to move to the other side of the patient and the third planned trajectory would be directed to a second side of the first vertebral body and the fourth planned trajectory would be directed to a second side of the second vertebral body. It should be noted, however, that the user may plan the surgical procedure in any order and the application 111 may be programmed to cause movement of the robotic arm 104 between the planned trajectories in the planned order.

The scalpel guide 160 may be provide with a body 165 having a first face 161, a second face 163, a first guide slot 162, a second guide slot 164, and a shoulder 166 extending outwardly from a portion of the body 165. The body 165 has a first central axis 167 extending through a center of the body The first guide slot 162 may be sized and shaped to receive the scalpel 190 and guide the scalpel 190 along a planned trajectory such as the planned trajectory 199. In some embodiments, the first guide slot 162 is sized and shaped to guide the scalpel 190 with insignificant lateral movement. The first guide slot 162 is defined by a first side 168, a second side 169 spaced apart from the first side 168, a third side 170, and a fourth side 171 spaced apart from the third side 170. The first guide slot 162 is arranged in the scalpel guide 160 such that a center (also referred to herein as a second central axis) of the first guide slot 162 aligns with the longitudinal axis 148 of the tool support 141 when the scalpel guide 160 is secured in the tool support 141 of the tool guide 140, the center of the first guide slot 162 being equidistant between the first side 168 and the second side 169 and equidistant between the third side 170 and the fourth side 171. The center of the first guide slot 162 is substantially coaxially aligned with the first central axis 167 of the body 165.

The second guide slot 164 may also be sized and shaped to receive the scalpel 190 and guide the scalpel 190 along a planned trajectory such as the planned trajectory 199. The second guide slot 164 may be provided with an upper portion 172 extending from the first face 144 to a lower end of the shoulder 166 and a lower portion 173 extending from the lower end of the shoulder 166 to the second face 146. The upper portion 172 may be provided with a guide slot 174 that is defined by a first side 175, a second side 176 spaced apart from the first side 175, a third side 177, and a fourth side 178 spaced apart from the third side 177. The guide slot 174 of the second guide slot 164 is arranged in the scalpel guide 160 such that a center of the guide slot 174 (also referred to herein as a third central axis) aligns with the longitudinal axis 148 of the tool support 141 when the scalpel guide 160 is secured in the tool support 141 of the tool guide 140, the center of the guide slot 174 being equidistant between the first side 175 and the second side 176 and equidistant between the third side 177 and the fourth side 178. The second guide slot 164 having the center (e.g., the third central axis) substantially coaxially aligned with the first central axis 167 of the scalpel guide 160 and the second central axis of the first guide slot 162.

The lower portion 173 of the second guide slot 164 may be provided with a channel 178 that extends across the body 165 of the scalpel guide 160 from the lower end of the shoulder 166 to the second face 146 of the scalpel guide 160 and is defined by a first side 179 and a second side 180 spaced apart from the first side 179. A trajectory plane 185 runs transversely through a center of the channel 178 and intersects the longitudinal axis 148 of the tool support 141 when the scalpel guide 160 is secured in the tool support 141 of the tool guide 140. The channel 178 is sized and shaped to direct the body 192 of the scalpel between the first side 179 and the second side 180 of the channel 178 which directs movement of the blade 194 of the scalpel 190 along the trajectory plane 185.

The size and shape of the first guide slot 162 is designed to only allow the scalpel 190 to move vertically along a Z axis (which may be referred to as a "vertical axis" for the purpose of illustration) while limiting horizontal movement of the scalpel 190 along an X axis and a Y axis. This allows a user (e.g., a surgeon) to use the first guide slot 162 to make a stab incision on the planned trajectory 199 using the scalpel 190.

Figure 4:
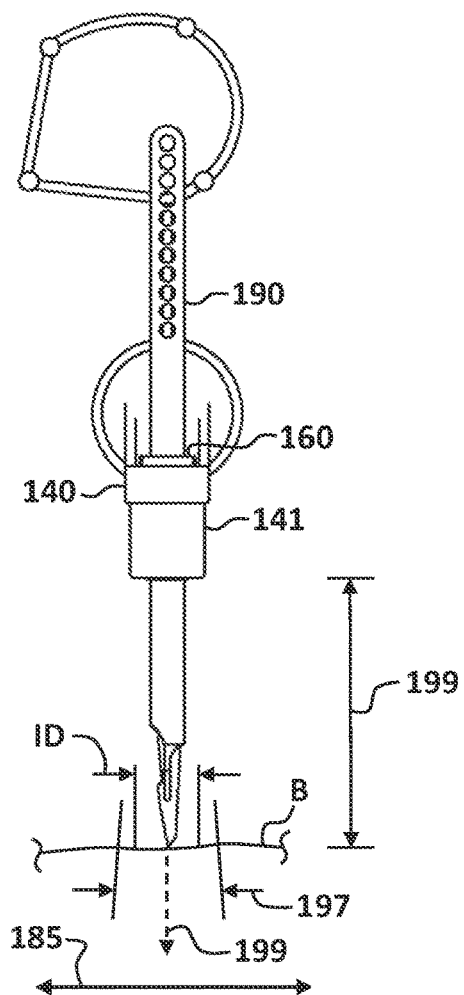
FIG. 4 is a front elevational view of the tool guide and scalpel guide of FIG. 1 with the scalpel inserted in the second guide slot of the scalpel guide such that a blade of the scalpel is directed along and restricted to a trajectory plane allowing an incision longer than an inner diameter of an aperture of the tool guide.

The size and shape of the second guide slot 164 is designed to allow the scalpel 190 to move vertically along the Z axis while also moving side-to-side or horizontally along the trajectory plane 185 (see FIG. 4). Because the scalpel guide 160 is rotatable in the tool support 141, the trajectory plane 185 may be aligned with anatomical structures of the patient such as a spinal column and/or muscle fibers to allow the user to open an incision that intersects the planned trajectory 199 to access the surgical site ST and expose patient anatomical structures such as a bone surface. As can be seen in FIG. 4, the size and shape of the second guide slot 164 allows an incision in the body B of the patient having a length 197 that is longer than an inside diameter ID of the aperture 142 of the tool support 141. The length 197 of the incision may be controlled by increasing or decreasing a height 198 between the second face 146 of the tool support 141 and the body B of the patient. For instance, an increase in the height 198 will result in a longer length 197 of the incision and a decrease in the height 198 will result in a shorter length 197 of the incision. It should be noted, however, that the user may make an incision that has a length 197 that is shorter than a total possible length 197 if desired. That is, the user may make an incision having a shorter length 197 if the user determines sufficient access to the anatomical structures of the patient may be gained using the shorter length 197.

In some embodiments, a transition (not shown) may be formed between the first side 175 and the second side 176 of the upper portion 172 and the channel 178 lower portion 173. At least a portion of the first side 175 and the second side 176 of the upper portion 172 may have a shape (e.g., arcuate or angled) that forms the transition and allows a wider range of movement of the scalpel 190 in the channel 178 along the trajectory plane 185.

In some embodiments, the scalpel guide 160 may be provided with the second guide slot 164 that is not separated into the upper portion 172 and the lower portion 173. In such an embodiment, the second guide slot 164 may be provided having the shape and dimension of the lower portion 173 of the second guide slot 164 described above extending from the first face 161 to the second face 163 of the scalpel guide 160. In such an embodiment, the second guide slot 164 would allow movement of the body 192 of the scalpel 190 horizontally along the trajectory plane 185 throughout the length of the second guide slot 164.

In use, a surgeon positions the scalpel guide 160 within the aperture 142 of the tool support 141 and aligns the longitudinal axis 148 with a planned trajectory. Then, the surgeon places the scalpel 190 within the first guide slot 162 and moves the scalpel 190 vertically along the axis 167 to form a stab incision in the patient. Then, the surgeon removes the scalpel 190 from the first guide slot 162 and places the scalpel 190 into the second guide slot 164. The surgeon moves the scalpel vertically until the scalpel 190 engages the patient, and then moves the scalpel 190 laterally along the trajectory plane 185 to widen the stab incision.

Figure 5A:
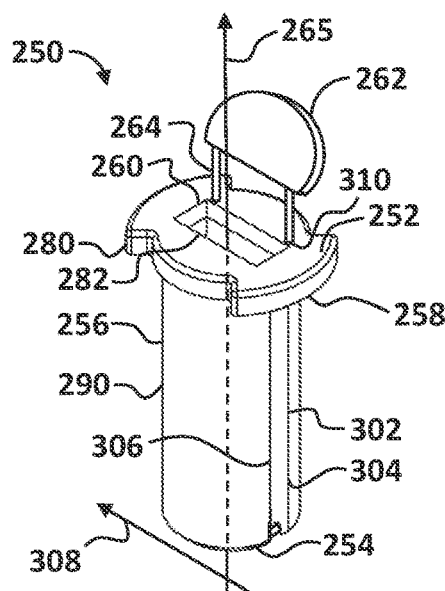
FIGS. 5A and 5B are perspective views of another scalpel guide having a variable guiding system constructed in accordance with one embodiment of the present disclosure.
Figure 5B:
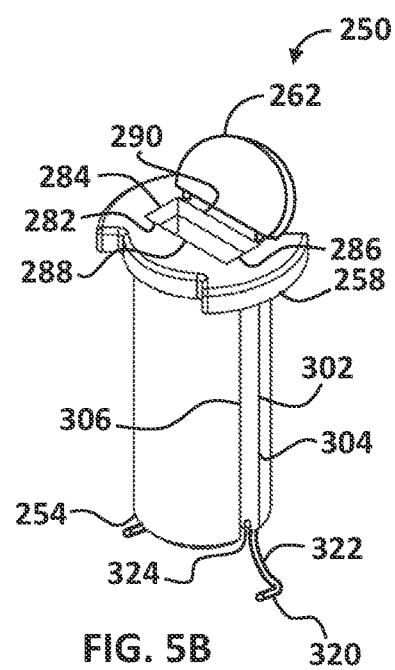

Referring now to FIGS. 5A and 5B, shown therein is a scalpel guide 250 having a variable guiding system. The scalpel guide 250 may be provided with a body 256 having a first face 252 (which may be referred to as "upper face 252"), a second face 254 (which may be referred to as "lower face 254"), a shoulder 258, a guide slot 260. The scalpel guide 250 also comprises a handle 262, and guide prongs 264 (only one of which is numbered) attached to and/or extending from the handle 262. The body 256 has a first central axis 265 extending through a center of the body 256.

The body 256 of the scalpel guide 250 may be sized and shaped to be received by the aperture 142 of the tool support 141 and secured within the tool support 141. The shoulder 258 extends outwardly from a portion of the body 256 and may be provided to contact the first face 144 of the tool support 141 when the scalpel guide 250 is secured in the tool support 141.

The guide slot 260 may be sized and shaped to receive the scalpel 190 and guide the scalpel 190 along a planned trajectory such as the planned trajectory 199. The guide slot 260 may be provided with an upper portion 280 extending from the first face 252 to the shoulder 258 and a lower portion 290 extending from the shoulder 258 to the second face 254.

The upper portion 280 of the guide slot 260 may be provided with a first guide slot 282 that is defined by a first side 284, a second side 286 spaced apart from the first side 284, a third side 288, and a fourth side 290 spaced apart from the third side 288. The first guide slot 282 extends through a central region within the scalpel guide 250 and is arranged in the scalpel guide 250 such that a center of the first guide slot 282 aligns with the longitudinal axis 148 of the tool support 141 when the scalpel guide 250 is secured in the tool support 141 of the tool guide 140, the center of the first guide slot 282 being equidistant between outer boundaries of the first side 284 and the second side 286 and equidistant between the third side 288 and the fourth side 290.

The lower portion 290 of the guide slot 260 may be provided with a channel 302 that extends across the body 256 of the scalpel guide 250 from the shoulder 258 to the second face 254 of the scalpel guide 250 and is defined by a first side 304 and a second side 306 spaced apart from the first side 304. A trajectory plane 308 runs transversely through a center of the channel 302 and intersects the longitudinal axis 148 of the tool support 141 when the scalpel guide 250 is secured in the tool support 141 of the tool guide 140. The channel 302 is sized and shaped to matingly engage and thereby direct the body 192 of the scalpel 190 to be moved laterally between the first side 304 and the second side 306 of the channel 302 which directs movement of the blade 194 of the scalpel 190 laterally solely along the trajectory plane 308.

The guide prongs 264 may be provided with a guide portion 320 (only one of which is numbered). The guide prongs 264 may be slidably inserted in apertures 310 (only one of which is numbered) that extend through the scalpel guide 250 from the first face 252 to the second face 254. The apertures 310 are positioned in the scalpel guide 250 aligned with the first side 284 and the second side 286 such that when the guide prongs 264 are in a first position where the handle 262 is positioned in an up position (illustrated in FIG. 5A), the apertures 310 arrange the guide portion 320 of the guide prongs 264 to direct the body 192 of scalpel 190 and limit movement of the scalpel 190 laterally along the trajectory plane 308. When the scalpel guide 250 is secured in the aperture 142 of the tool support 141 and the guide prongs 264 are in the first position, the guide prongs 264 engage both sides of the scalpel 190 to restrict lateral movement of the blade 194 of the scalpel 190. Thus, the blade 194 of the scalpel 190 is directed only along the planned trajectory 199 to allow a stab incision to be performed on the planned trajectory 199. In the first position, the guide portion 320 of the guide prongs 264 may be in contact with the second face 254 of the scalpel guide 250. In some embodiments, the second face 254 may be provided with a notch 324 (only one of which is numbered) sized and shaped to at least partially receive and nest the guide portion 320 of the guide prongs 264 when the guide prongs 264 are in the first position.

The guide prongs 264 are illustrated as extending at a substantially right-angle from a body 322 (only one of which is numbered) of the guide prongs 264. However, it should be noted that the guide prongs 264 may be provided having other arrangements or angles so long as the guide prongs 264 extend substantially across the channel 302 to direct the body 192 of the scalpel 190 as described above.

In a second position where the handle 262 is positioned in a down position (illustrated in FIG. 5B), the guide portion 320 of the guide prongs 264 are moved away from the second face 254 to permit restricted lateral movement of the blade 194 of the scalpel 190 to allow an incision to be made that intersects the planned trajectory 190. As the scalpel 190 is moved laterally, the scalpel 190 engages the guide prongs 264 to restrict lateral movement of the scalpel 190 along the trajectory plane 308. In some embodiments, a spring bias of the guide prongs 264 pushes the guide portion 320 away from a center of the scalpel guide 250. In the second position, when the scalpel 190 is inserted in the guide slot 260 the channel 302 guides the body 192 of the scalpel 190 laterally along the trajectory plane 308 allowing an incision to be made that intersects with the planned trajectory 199 but that is longer than the inside diameter ID of the aperture 142 of the tool support 141. In some embodiments, the trajectory plane 308 extends transversely substantially through a center of the channel 302.

The guide prongs 264 may be moved between the first and second positions by pushing or pulling on the handle 262 allowing the user (e.g., a surgeon) to make a stab incision along the planned trajectory 199 and/or an incision that intersects with the planned trajectory 199 but that may be longer than the inside diameter ID of the aperture 142 of the tool support 141.

The guide prongs 264 may be made of any known material that is biocompatible, resists deformation and has a tendency to return to its original shape once applied forces such as compression, tension, etc. have been removed. For instance, the guide prongs 264 may be formed from spring steel.

In use, a surgeon positions the scalpel guide 250 within the aperture 142 of the tool support 141 and aligns the longitudinal axis 148 with a planned trajectory. The surgeon moves the guide prongs 264 to the first position and then places the scalpel 190 within the guide slot 260. The surgeon then moves the scalpel 190 vertically along the axis 265 to form a stab incision in the patient. Then, the surgeon moves the guide prongs 264 to the second position and then moves the scalpel 190 laterally along the trajectory plane 308 to widen the stab incision.

Figure 6A:
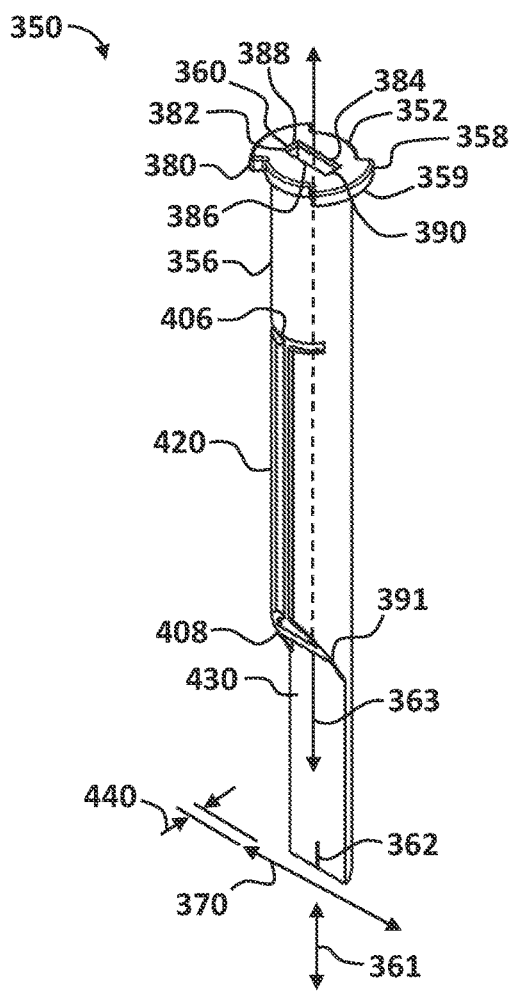
FIGS. 6A and 6B are perspective views of another scalpel guide constructed in accordance with the present disclosure and having an elongated portion with a trajectory marker formed therein that indicates a planned trajectory and a guide slot sized and shaped to allow a scalpel to be moved laterally only along an arc on a single-plane that intersects the planned trajectory.
Figure 6B:
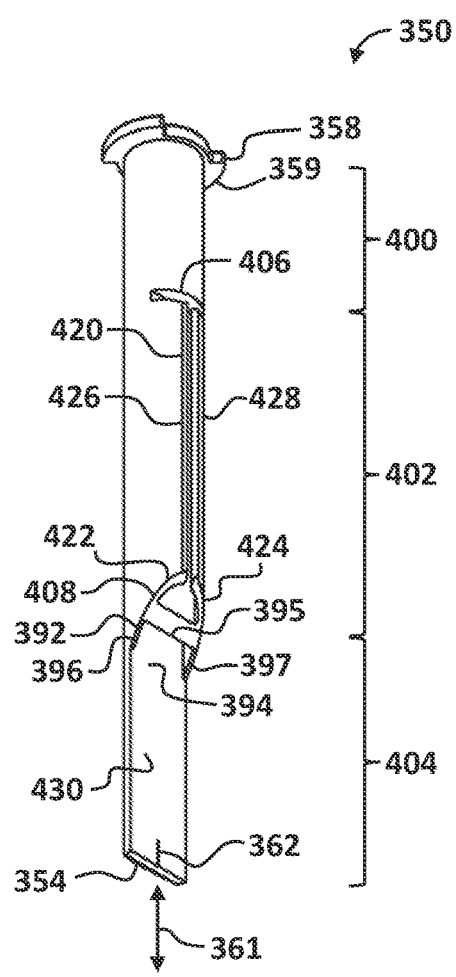

Referring now to FIGS. 6A and 6B, shown therein is a scalpel guide 350. The scalpel guide 350 may be provided with a body 356 having a first face 352 (which may be referred to as "first end 352"), a second face 354 (which may be referred to as a "second end 354"), a shoulder 358, a guide slot 360, and a trajectory marker 362 formed in the body 356.

The shoulder 358 extends outwardly from a portion of the body 356 and may be provided to contact the first face 144 of the tool support 141 when the scalpel guide 350 is secured in the tool support 141. The shoulder 358 may be provided having a predetermined depth that extends from the first face 352 to a lower face 359 of the shoulder 358. The body 356 may also have a central axis 363 extending through a center of the body 356.

The guide slot 360 may be sized and shaped to receive the scalpel 190 and guide the scalpel 190 laterally along a trajectory plane 370 that intersects with a planned trajectory such as the planned trajectory 199. The guide slot 360 may be provided with an upper portion 380 extending from the first face 352 to the lower surface 359 of the shoulder 358 and a lower portion 391 extending from the lower surface 359 of the shoulder 358 to the elongated section 368 of the body 356.

The upper portion 380 may be provided with a first guide slot 382 that is defined by a first side 384, a second side 386 spaced apart from the first side 384, a third side 388, and a fourth side 390 spaced apart from the third side 388. In some embodiments, the first guide slot 382 extends along the central axis 363 and through a central region within the scalpel guide 350 and is arranged in the scalpel guide 350 such that the central axis 363 aligns with the longitudinal axis 148 of the tool support 141 when the scalpel guide 350 is secured in the tool support 141 of the tool guide 140, the central axis 363 being equidistant between outer boundaries of the first side 384 and the second side 386 and equidistant between the third side 388 and the fourth side 390.

The lower portion 391 of the guide slot 360 may be provided with an opening 392 defined by a first side 394, a second side 395 spaced apart from the first side 394, a third side 396, and a fourth side 397 spaced apart from the third side 396. The guide slot 360 extends through the central region within the scalpel guide 350 and is arranged in the scalpel guide 350 such that a central axis of the second guide slot 392 aligns with the longitudinal axis 148 of the tool support 141 when the scalpel guide 350 is secured in the tool support 141 of the tool guide 140, the central axis of the second guide slot 392 being equidistant between outer boundaries of the first side 394 and the second side 395 and equidistant between the third side 396 and the fourth side 397. The opening 392 may be wider from when measured from the third side 396 to the fourth side 397 than the first guide slot 382 when measured from the third side 388 to the fourth side 390. In other words, the guide slot 360 is tapered from the upper portion 380 to the lower portion 391 and is sized and shaped to direct the body 192 of the scalpel 190 between the first side 394 and the second side 395 of the opening 392 to allow the scalpel 190 to move on an arc to allow a single-plane incision to be made along the trajectory plane 370 that is longer than an inside diameter of the tool support 141.

In some embodiments, the scalpel guide 350 may be provided with the guide slot 360 that is not separated into the upper portion 380 and the lower portion 391. In such an embodiment, the guide slot 360 may be provided having the shape and dimension of the opening 392 described above extending from the first face 352 to the elongated section 368 of the body 356. In such an embodiment, the guide slot 360 would allow movement of the body 192 of the scalpel 190 horizontally, i.e., laterally, along the trajectory plane 370 throughout the length of the guide slot 360.

The body 356 may be provided with a seat section 400, a tension section 402, an elongated portion 404, and an insertion marker 406. Optionally, the body may be provided with an angled portion 408 at a lower end of the tension section 402.

The seat section 400 of the body 356 extends from the shoulder 358 to the insertion marker 406 and may be sized and shaped to be received by the aperture 142 of the tool support 141 and secured within the tool support 141. In the illustrated embodiment of the scalpel guide 350, the seat section 400 is cylindrical and has an outer diameter that is substantially the same as an inner diameter of the aperture 142 of the tool support 141. It should be noted, however, that the seat section 400 may be formed having any shape and/or size associated with the aperture 142 of the tool support 141.

The tension section 402 extends from the insertion marker 406 to the elongated portion 404 and may be provided with a tension element 420 designed to hold tension between the scalpel guide 350 and the aperture 142 of the tool support 141 when the scalpel guide 350 is partially inserted into the aperture 142 of the tool support 141 such that the scalpel guide 350 may be positioned at a desired depth in the aperture 142 of the tool support 141.

In the illustrated embodiment, the tension element 420 is provided with a first spring element 422 and a second spring element 424. The first spring element 422 may be provided with a first protrusion 426 and the second spring element 424 may be provided with a second protrusion 428, the first and second protrusions 426 and 428 extending beyond an outer diameter of the seat section 400 such that when the scalpel guide 350 is inserted into the aperture 142 of the tool support 141 the first and second protrusions 426 and 428 contact an inner surface of the aperture 142 and compress the first spring element 422 and the second spring element 424 to provide tension between the scalpel guide 350 and the aperture 142 of the tool support 141.

In the illustrated embodiment of the scalpel guide 350, the first and second spring elements 422 and 424 are generally rounded and follow the outer diameter of the seat section 400. However, it should be noted that the first and second spring elements 422 and 424 may be provided having any shape and/or form that allows the first and second spring elements 422 and 424 to provide tension between the scalpel guide 350 and the aperture 142 of the tool support 141 as described herein. The first and second spring elements 422 and 424 may be made of any known or future developed material that resists deformation and has a tendency to return to its original shape once applied forces such as compression, tension, etc. have been removed. For example, the first and second spring elements 422 and 424 may be constructed of composite plastic or spring steel.

The elongated portion 404 may be provided with a marker surface 430 having the trajectory marker 362 formed therein. The marker surface 430 may be an extension of the first side 394 of the lower portion 391 of the guide slot 360. The marker surface 430 may be offset from the trajectory plane 370 a predetermined distance 440. The predetermined distance 440 may be designed to align the blade 194 of the scalpel 190 with the trajectory plane 370. In some embodiments, for instance, the predetermined distance 440 may be half the width of the body 192 of the scalpel 190 and may be aligned with the blade 194 of the scalpel 190. In some embodiments, the width of the body of the scalpel may be 4 millimeters (mm) and the predetermined distance 440 may be 2 mm.

The trajectory marker 362 may be aligned with but offset from the central axis 361 of guide slot 360 which is coaxially aligned with the planned trajectory 199 when the scalpel guide 350 is inserted in the aperture 142 of the tool support 141. The trajectory marker 362 is offset from the central axis 361 of the guide slot 360 by the predetermined distance 440.

In an exemplary usage of the scalpel guide 350, the scalpel guide 350 may be inserted in the aperture 142 of the tool support 141 which is aligned with the planned trajectory 199. A user (e.g., a surgeon) may use the trajectory marker 362 to mark an intersection of the planned trajectory 199 and the body B of the patient. The user may mark the intersection of the planned trajectory 199 and the body B of the patient using a marking device (e.g., a marking pen) and making a mark on the body B of the patient in line with the trajectory marker 362 offset by the predetermined distance 440 from the marker surface 430. Alternatively, the user may use the scalpel 190 to make a stab incision in the body B of the patient by inserting the scalpel 190 in the guide slot 360 and aligning a point of the blade 194 of the scalpel 190 with the trajectory marker 362.

The user may also use the scalpel 190 to open an incision that intersects the planned trajectory 199 to access the surgical site ST and expose patient anatomical structures such as a bone surface. For instance, the user may align the marker surface 430 with the anatomical structures of the patient and use the scalpel 190 to make a single-plane incision along the trajectory plane 370 that may be longer than an inside diameter of the tool support 141.

To assist in insertion of the scalpel guide 350 into the aperture 142, the scalpel guide 350 may be provided with the angled portion 408 that provides a transition between the elongated portion 404 and the tension section 402. For instance, the angled portion 408 may extend from the marker surface 430 at a predetermined angle up and back through the tension section 402. The predetermined angle may be between twenty-five degrees (25°) and sixty degrees (60°). In an exemplary embodiment, the predetermined angle may be forty-five degrees (45°).

In some embodiments, the scalpel guide 350 may be used as a tissue retractor once an incision has been made in the body B of the patient. In an exemplary usage of the scalpel guide 350, the scalpel guide 350 may be inserted in the aperture 142 of the tool support 141 which is aligned with the planned trajectory 199. A user (e.g., a surgeon) may use the trajectory marker 362 to mark an intersection of the planned trajectory 199 and the body B of the patient. The user may mark the intersection of the planned trajectory 199 and the body B of the patient using a marking device (e.g., a marking pen) and making a mark on the body B of the patient in line with the trajectory marker 362 offset by the predetermined distance 440 from the marker surface 430. The user may then at least partially withdraw the scalpel guide 350 in the aperture 142 and make an incision in the body B of the patient through the mark. The scalpel guide 350 may then be inserted and/or advanced in the aperture 142 and the elongated portion 404 may be inserted into the incision and used to retract the tissue of the patient to expose anatomical structures of interest such as the spinal column.

From the above description, it is clear that the inventive concept(s) disclosed herein are well adapted to carry out the objects and to attain the advantages mentioned herein, as well as those inherent in the inventive concept(s) disclosed herein. While the embodiments of the inventive concept(s) disclosed herein have been described for purposes of this disclosure, it will be understood that numerous changes may be made and readily suggested to those skilled in the art which are accomplished within the scope and spirit of the inventive concept(s) disclosed herein.

What is claimed is:
1. A scalpel guide, comprising
  a body having a first face and a second face, the body sized and shaped to be at least partially inserted into an aperture of a tool guide of a surgical system, the body having a shoulder extending outwardly from a portion of the body, the shoulder having a lower face, the body having a first central axis extending through a center of the body, the body having an outer peripheral surface extending from the upper face to the lower face;

the body having spaced apart first side and a second side forming a first guide slot extending through the body from the first face to the second face, the first guide slot having a second central axis substantially coaxially aligned with the first central axis of the body, the first guide slot sized and shaped to receive a body of a scalpel and guide a blade of the scalpel along the second central axis; and the body having spaced apart sides forming a second guide slot having a third central axis substantially coaxially aligned with the first central axis of the scalpel guide and the second central axis of the first guide slot, the second guide slot having an upper portion and a lower portion, the upper portion of the second guide slot formed in and extending through the body and the shoulder from the first face of the body to the lower face of the shoulder and not intersecting the outer peripheral surface of the body, the lower portion having a channel extending through the body from the lower face of the shoulder to the second face of the body with sides of the channel defined by opposing sides, the channel defining a trajectory plane that extends through a center of the channel transversely and intersects the third central axis, wherein the second guide slot is arranged such that the body of the scalpel inserted in the second guide slot is guided vertically by the sides of the second guide slot and allowed to move horizontally across the channel along the trajectory plane.

2. The scalpel guide of claim 1, wherein the second guide slot intersects the first guide slot and is arranged in an orthogonal orientation relative to the first guide slot.

3. The scalpel guide of claim 1, wherein the second guide slot intersects the outer peripheral surface of the body.

4. The scalpel guide of claim 1, wherein the outer peripheral surface of the body matingly is configured to matingly engage an inner surface of the tool guide, the inner surface of the tool guide defining the aperture.

5. A scalpel guide, comprising
a body having an first face and a second face, the body sized and shaped to be at least partially inserted into an aperture of a tool guide of a surgical system, the body having a shoulder extending outwardly from the body, the body having a first central axis extending through a center of the body;

the body having internal sides defining a guide slot, the guide slot aligned with the first central axis of the scalpel guide;

a handle having a first guide prong and a second guide prong extending therefrom, the first guide prong and the second guide prong constructed of a spring bias material, the first guide prong and the second guide prong slidably inserted in first and second apertures within the body, the first guide prong having a first guide portion and the second guide prong having a second guide portion, the first guide portion and the second guide portion spaced apart and extending across at least a portion of the guide slot; and wherein when the handle is in a first position the first guide portion and the second guide portion are positioned adjacent to the guide slot to restrain a scalpel positioned in the guide slot from horizontal movement, and when the handle is in a second position, the first and second guide portions are positioned away from the guide slot to permit horizontal movement for a scalpel positioned in the guide slot.

6. The scalpel guide of claim 5, wherein the shoulder extends from the first face of the body to a lower face of the shoulder.

7. The scalpel guide of claim 5, wherein the guide slot has an upper portion and a lower portion, the upper portion formed in and extending through the body and the shoulder from the first face of the body to the lower face of the shoulder, the upper portion sized and shaped to receive a body of a scalpel, the lower portion having a channel extending through the body in a region between the lower face of the shoulder to the second face of the body with sides of the channel defined by a first side and a second side opposite the first side, the channel defining a trajectory plane that extends transversely substantially through a center of the channel.

8. The scalpel guide of claim 5, wherein the first guide prong has a first bend adjacent to the first guide portion, and the second guide prong has a second bend adjacent to the second guide portion, and wherein the first bend in the first guide prong and the second bend in the second guide prong are substantially right-angle bends.

9. The scalpel guide of claim 5, wherein the first and second apertures extend through the upper face of the body.

10. The scalpel guide of claim 5, wherein the body has an outer peripheral surface, and wherein the channel intersects the outer peripheral surface.

11. The scalpel guide of claim 5, wherein the one or more internal sides defining the guide slot extend through the body from the first face to the second face.

12. A robotic surgical system, comprising:
a robotic arm;
a tool guide supported by the robotic arm, the tool guide comprising a tool support having a first end, a second end, an aperture extending through the tool support from the first end to the second end, and a longitudinal axis extending through a center of the aperture from the first end to the second end; and
a controller in communication with the robotic arm, the controller having a non-transitory computer readable memory and a processor, the non-transitory computer readable memory storing at least one planned trajectory associated with a surgical procedure and processor executable instructions that, when executed, cause the processor to pass a first signal to the robotic arm causing the robotic arm to position the tool support a distance from a patient with the longitudinal axis of the tool support substantially coaxially aligned with the at least one planned trajectory; and
a scalpel guide comprising:
a body having a first end, a second end opposite the first end, a guide slot extending between the first end and the second end, and a central axis extending through a center of the body,
the body including a shoulder at the first end of the body and extending outwardly from a portion of the body and extending from the first end to a lower face of the shoulder;
the guide slot being formed in and extending through the body from the first end to the second end, the guide slot defined by a first face, a second face opposite the first face, a third face, and a fourth face opposite the third face, the guide slot having a second central axis substantially coaxially aligned with the central axis of the scalpel guide, the guide slot defining a trajectory plane that extends through a center of the guide slot parallel with the first face and the second face and intersecting the second central axis;

the body further comprising:

a seat section extending from the lower face of the shoulder to an insertion marker formed in the body, the seat section sized and shaped to be at least partially inserted into the aperture of the tool guide of the robotic surgical system; and an elongated portion extending from the second end toward the seat section, the elongated portion having a marker surface that is an extension of the first face of the guide slot, the marker surface having a trajectory marker formed therein, the trajectory marker aligned with the central axis of the scalpel guide and offset a predetermined distance from the trajectory plane.

13. The robotic surgical system of claim 12, wherein the scalpel guide further comprises a tension section between the seat section and the elongated portion, the tension section having a tension element configured to hold tension between the body and the tool guide when the tension section is positioned within the aperture of the tool guide.

14. The robotic surgical system of claim 13, wherein the tension section further comprises an angled portion that extends from the marker surface of the elongated portion at a predetermined angle up through tension section.

15. The robotic surgical system of claim 12, wherein the predetermined distance the trajectory marker is offset from the trajectory plane is half of a width of a body of a scalpel.

16. The robotic surgical system of claim 15, wherein the width of the body of the scalpel is 4 millimeters.

* * * * *